United States Patent
Winsett et al.

(10) Patent No.: US 9,187,384 B2
(45) Date of Patent: Nov. 17, 2015

(54) PRODUCTION OF ALKYLAROMATIC COMPOUNDS

(75) Inventors: Beth A. Winsett, Houston, TX (US); James I. Arnett, II, Greenwell Springs, LA (US); Kenwyn M. Leger, Pride, LA (US); Brady A. Compton, Baton Rouge, LA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 241 days.

(21) Appl. No.: 13/324,176

(22) Filed: Dec. 13, 2011

(65) Prior Publication Data

US 2013/0150608 A1  Jun. 13, 2013

(51) Int. Cl.

| | |
|---|---|
| C07C 2/66 | (2006.01) |
| C07C 7/04 | (2006.01) |
| C07C 17/383 | (2006.01) |
| C07C 37/76 | (2006.01) |
| C07C 41/42 | (2006.01) |
| C07C 45/82 | (2006.01) |
| C07C 67/54 | (2006.01) |
| C07C 68/08 | (2006.01) |
| C07C 201/16 | (2006.01) |
| C07C 209/84 | (2006.01) |
| C07C 319/28 | (2006.01) |
| C07C 201/12 | (2006.01) |
| C07C 209/68 | (2006.01) |
| C07C 37/14 | (2006.01) |
| C07C 7/05 | (2006.01) |

(52) U.S. Cl.
CPC ... *C07C 7/04* (2013.01); *C07C 2/66* (2013.01); *C07C 7/05* (2013.01); *C07C 17/383* (2013.01); *C07C 37/14* (2013.01); *C07C 201/12* (2013.01); *C07C 201/16* (2013.01); *C07C 209/68* (2013.01); *C07C 209/84* (2013.01); *C07C 319/28* (2013.01)

(58) Field of Classification Search
None
See application file for complete search history.

(56) References Cited

U.S. PATENT DOCUMENTS

| | | | |
|---|---|---|---|
| 2,541,044 A | | 2/1951 | Daugherty |
| 2,652,435 A | * | 9/1953 | Hess et al. ............... 585/816 |
| 4,211,665 A | | 7/1980 | Pellegrini, Jr. |
| 4,238,343 A | | 12/1980 | Pellegrini, Jr. |
| 4,301,316 A | | 11/1981 | Young |
| 4,570,027 A | | 2/1986 | Boucher et al. |
| 4,604,491 A | | 8/1986 | Dressler et al. |
| 4,665,275 A | | 5/1987 | Yoshida et al. |
| 4,714,794 A | | 12/1987 | Yoshida et al. |
| 4,737,297 A | | 4/1988 | Yoshida et al. |
| 5,019,670 A | | 5/1991 | Lê et al. |
| 5,034,563 A | * | 7/1991 | Ashjian et al. ............ 585/455 |
| 5,177,284 A | | 1/1993 | Le et al. |
| 5,191,135 A | | 3/1993 | Dwyer et al. |
| 5,254,274 A | | 10/1993 | Ho et al. |
| 5,342,532 A | | 8/1994 | Takei et al. |
| 5,602,086 A | | 2/1997 | Le et al. |
| 2008/0161620 A1 | | 7/2008 | Bozzano et al. |

FOREIGN PATENT DOCUMENTS

| | | |
|---|---|---|
| EP | 0 818 432 | 1/1998 |
| EP | 1 020 417 | 7/2000 |

OTHER PUBLICATIONS

Zygula, "A Design Review of Steam Stripping Columns for Wastewater Service," KLM Technology Group, Apr. 2007; Obtained from <http://www.klmtechgroup.com/Technical%20Articles.htm> Accessed Mar. 24, 2014.*

* cited by examiner

*Primary Examiner* — Alicia L Otton

(57) ABSTRACT

This invention is directed to an improvement in the process for the production of alkylaromatic compounds that results in lower levels of residual unreacted materials in the final product. This invention comprises: 1) alkylation of an aromatic compound with an alkylating agent and a catalyst to produce an effluent stream comprising an alkylaromatic compound and unreacted materials; 2) heating the effluent stream; 3) stripping the effluent stream in a stripping device in the presence of steam; 4) separating a stripping stream from the stripping device, the stripping stream rich in unreacted materials; and 5) separating a product stream from the stripping device, the product stream rich in alkylated aromatic compound.

6 Claims, No Drawings

PRODUCTION OF ALKYLAROMATIC COMPOUNDS

FIELD OF THE INVENTION

This disclosure relates to an improved process for the production of alkylaromatic compounds.

BACKGROUND

Alkylaromatic compounds have been known for many years. They possess good thermal and oxidative stabilities, as disclosed in U.S. Pat. Nos. 4,211,665; 4,238,343; 4,604,491; and 4,714,794. Improvements have been made to the compounds over the years. U.S. Pat. Nos. 5,254,274 and 5,019,670, for example, disclose methods of improving the thermal and oxidative stabilities of PAOs by alkylating unsaturated oligomers with an aromatic compound. The products have improved stability and solvency due to the aromatic component as well as improved rheological characteristics. U.S. Pat. Nos. 4,737,297; 4,714,794; and 4,665,275 disclose various monoalkylate compounds with good oxidative stability and U.S. Pat. No. 5,342,532 discloses a mono- or dialkylate benzothiophene with good oxidative stability. U.S. Pat. No. 5,177,284 discloses making an alkylated naphthalene fluid with improved thermal and oxidative stability using low alkylation temperatures and low acidity zeolite catalysts. U.S. Pat. No. 5,602,086 discloses blends of alkylaromatics with PAOs to improve oxidation stability, solubility, elastomer compatibility, and hydrolytic stability.

Alkylaromatic compounds may be produced by the alkylation of a suitable aromatic compound in the presence of an alkylating agent and an alkylation catalyst such as a Friedel-Krafts catalyst, an acidic clay as described in U.S. Pat. Nos. 4,714,794 and 4,604,491, or a Lewis acid such as aluminum trichloride as described in U.S. Pat. Nos. 4,211,665 and 4,604,491. U.S. Pat. No. 4,570,027 describes the use of a catalyst described as a collapsed silica-alumina zeolite. Various other zeolites may also be used, such as zeolite L, ZSM-4, and ZSM-5 as disclosed in U.S. Pat. No. 4,301,316, zeolite MCM-22 as disclosed in U.S. Pat. No. 5,019,670, or zeolites USY and Beta as described in U.S. Pat. No. 5,177,284.

In current processes to produce alkylaromatic compounds, a residual amount of unreacted aromatic compound and alkylating agent remains in the reactor effluent. It is advantageous to minimize the amount of unreacted material in the reactor effluent to maximize yield of desired product. It is also desirable to minimize the amount of unreacted aromatic compound remaining because industry regulations limit the amount of this material that may be present in finished products. It has been known to apply a batch stripping process to the alkylated compound to strip unreacted aromatic compound from the product. Following this batch stripping process, some amount of unreacted aromatic compound still remains in the product. An improved process to strip further amounts of unreacted aromatic compound from the final product would be advantageous for the reasons cited above.

SUMMARY OF THE INVENTION

This invention is directed to an improved process for the production of alkylaromatic compounds. Specifically, this invention is directed to a process that surprisingly results in low levels of residual unreacted aromatic compound and alkylating agent in the final product. This invention comprises:

1) alkylation of an aromatic compound with an alkylating agent and a catalyst to produce an effluent stream comprising an alkylaromatic compound and unreacted materials;
2) heating said effluent stream to between 100 and 250° C.;
3) in a stripping device maintained at a vacuum pressure of 5 mmHg to 760 mmHg, stripping said heated effluent stream in the presence of steam, wherein the steam to effluent stream feed ratio is from 0.05 to 1;
4) separating a stripping stream from said stripping device, said stripping stream rich in unreacted alkylatable aromatic compound, unreacted alkylating agent, and optionally monoalkylate product; and
5) separating a product stream from said stripping device, said product stream rich in alkylated aromatic compound.

The stripping step occurs in the presence of steam, where it is believed that the steam continuously shifts the liquid/vapor phase equilibrium in each of the tower stages, thus driving greater amounts of unreacted materials into the vapor phase so that they can be removed. This advantageously results in low levels of residual unreacted aromatic compound and alkylating agent in the final product.

DETAILED DESCRIPTION OF THE INVENTION

In general, this invention involves alkylating an aromatic compound in the presence of an alkylating agent and a catalyst. The product of this reaction is a reactor effluent comprising an alkylaromatic compound and unreacted materials, which is then stripped in a stripping device in the presence of steam. A stripping stream is separated from the stripping device, said stripping stream being rich in unreacted materials and optionally monoalkylate product. A product stream is also separated from the stripping device, said product stream being rich in alkylated aromatic compound. The stripping stream, or any portion thereof, may be recycled back into the alkylation reaction.

For purposes of this invention, when a stream is said to be "rich" in a component, "rich" is defined to mean that the concentration of that component is higher in the stream than it was in the reactor effluent prior to stripping. For example, when the stripping stream is said to be "rich" in unreacted alkylated aromatic compound, it means that the concentration of this compound is higher in the stripping stream that it was in the reactor effluent prior to stripping.

Aromatic Compound

The starting materials for the production of the alkylated compound include any alkylatable aromatic compound, but preferably naphthalene, methylnaphthalenes, or substituted naphthalenes. Substituted naphthalenes may contain one or more short chain alkyl groups containing up to about eight carbon atoms, such as methyl, ethyl, or propyl. Suitable alkyl-substituted naphthalenes include alpha-methylnaphthalene, dimethylnaphthalene, and ethylnaphthalene.

Alkylating Agent

Suitable alkylating agents include any aliphatic or aromatic organic compound having one or more available alkylating aliphatic group capable of alkylating the naphthalene. The alkylating aliphatic group itself should have at least 6 carbon atoms, and preferably at least 10. Olefins containing from 2 to about 30 carbon atoms such as ethylene, propylene, butene, pentene, hexene, octene, decene, dodecene, tetradecene, and the like may be used. Branched olefins, such as trimers, tetramers, pentamers, etc. of light olefins such as ethylene, propylene, butylenes, etc. may also be used. Mixtures of such olefins may also be used. Other alkylating agents which may be used, although less easily, include alcohols (including monoalcohols, dialcohols, trialcohols, etc.) such as hexanols, heptanols, octanols, decanols, undecanols, and dodecanols; and alkyl halides such as hexyl chlorides, octyl chlorides, dodecyl chlorides; and higher homologs. However, the alkylating agents are most preferably linear alpha olefins (LAOs) containing from 8 to 18 carbon atoms including mixtures thereof. In an embodiment of the invention, the alkylating agent is at least one LAO selected from the group including 1-octene, 1-decene, 1-dodecene, 1-tetradecene, 1-hexadecene, and 1-octadecene.

Catalyst

The alkylation process is carried out in the presence of a catalyst, and any catalyst known in the art may be used. Preferred catalysts include zeolite catalysts. The molecular size of the alkylation compounds requires a relatively large pore size in the zeolite for the products to leave the zeolite. Useful zeolites may be characterized by the presence of 12-membered oxygen rings in the molecular structure and a constraint index of not more than 2, and in most cases not more than 1. A method for determining constraint index, the significance of the index, and values of typical zeolites is described in U.S. Pat. Nos. 4,016,218 and 4,861,932, to which reference is made for such details. Examples of zeolites that may be useful include faujasite, the synthetic faujasites (zeolites X and Y, U.S. Pat. Nos. 2,882,244 and 3,130,007, respectively), zeolite L, ZSM-4 (U.S. Pat. No. 3,923,639), ZSM-18 (U.S. Pat. No. 3,950,496), ZSM-20 (U.S. Pat. No. 3,972,983), zeolite beta, and mordenite and offretite.

Some intermediate pore size zeolites with 10-membered oxygen rings may be useful if their structure is not too highly constrained. Thus, zeolites such as ZSM-12 (constraint index is 2; U.S. Pat. No. 3,948,758) may be useful. MCM family zeolites may also be useful, including for example, MCM-22/alumina (U.S. Pat. No. 5,019,670), MCM-49/alumina (U.S. Pat. No. 5,236,575), MCM-56/alumina (U.S. Pat. No. 5,362,697), etc. Thus, zeolites having a constraint index up to about 3 may be useful, although the activity may be dependent on the choice of alkylating agent, especially its chain length, a factor which imposes diffusion limitations on the choice of zeolite.

A highly useful zeolite is zeolite Y, and especially zeolite Y in the ultrastable form, usually referred to as USY. Zeolite USY is produced by the stabilization of zeolite Y by a procedure of repeated ammonium exchange and controlled steaming. Processes for the production of zeolite USY are described in U.S. Pat. Nos. 3,402,966; 3,923,192; and 3,449,070.

All of the patents referenced herein describing catalysts are incorporated herein by reference for the details of such descriptions.

The zeolite may be composited with a matrix material or binder which is resistant to the temperatures and other conditions employed in the alkylation process. Such materials include active and inactive materials and synthetic or naturally occurring zeolites as well as inorganic materials such as clays, silica and/or metal oxides such as alumina, silica or silica-alumina. The latter may be either naturally occurring or in the form of gelatinous precipitates or gels including mixtures of silica and metal oxides. Use of an active material in conjunction with the zeolite may change the conversion and/or selectivity of the catalyst. Inactive materials suitably serve as diluents to control the amount of conversion so that alkylation products can be obtained economically and orderly without employing other means for controlling the rate of reaction. Binders which may be incorporated to improve the crush strength and other physical properties of the catalyst under commercial alkylation operating conditions include naturally occurring clays, e.g., bentonite and kaolin as well as the oxides referred to above.

The catalyst wt % in the overall feed may vary widely, ranging from about 0.1 to about 90 wt %. In an embodiment of the invention, the catalyst wt % in the overall feed is less than 10 wt %, less than 8 wt %, less than 6 wt %, or less than 4 wt %. In an embodiment of the invention, the catalyst wt % in the overall feed is between 0.5 and 10 wt %, 0.5 and 8 wt %, 0.5 and 6 wt %, or 0.5 and 4 wt %. Prior to use in the reaction, the stability of the catalyst may be increased by steaming U.S. Pat. Nos. 4,663,492; 4,594,146; 4,522,929; and 4,429,176 describe conditions for the steam stabilization of zeolite catalysts, to which reference is made for description of such conditions.

Alkylation Process

The alkylation reaction may be carried out in a number of suitable reaction zones, such as batch-type typically employing a closed, pressurized, stirred reactor with an inert gas blanketing system, or a semi-continuous or continuous operation utilizing a fixed, fluidized, or moving bed catalyst system, such as a flow reactor containing a fixed bed of the catalyst composition. The reactants can be in either the vapor or the liquid phase and can be free from intentional admixture or dilution, or they can be brought into contact with the catalyst with the aid of carrier gases or diluents such as, for example, hydrogen or nitrogen.

Reaction conditions for the alkylation reaction may comprise temperatures between −30 and 500° C., more typically between 30 and 250° C., pressures between 20 and 25,000 kPa, and a feed weight hourly space velocity (WHSV) of from about $0.1\ hour^{-1}$ to $100\ hour^{-1}$, more typically from about $0.5\ hour^{-1}$ to $10\ hour^{-1}$. The WHSV is based upon the total weight of active catalyst (and binder, if present). When using naphthalene as the aromatic compound, the pressure should be maintained at at least about 350 kPa to prevent the naphthalene from subliming into the overhead of the alkylation reactor. The molar ratio of alkylating agent to aromatic compound may range from 0.1:1 to 10:1, typically from 1:1 to 5:1. In a preferred embodiment of the invention, it is at least 2:1.

The continuous stripping may be carried out in a multiple-stage stripping device. Continuous stripping is defined as stripping in which a feed, usually of nearly constant composition, is supplied continuously to a fractionating column, and the product is continuously withdrawn at the top, the bottom, and sometimes intermediate points. In the invention, "stripping" and "distillation" are considered interchangeable terms and processes.

In this invention, a multi-stage stripping device may be used with steam, wherein steam is thought to shift the liquid/vapor phase equilibrium at each stage in the tower, enabling greater amounts of unreacted materials to be removed. The steam continuously dilutes the vapor phase concentrations of unreacted materials, and monoalkylate if desired, thus providing a constant driving force for these materials to vaporize out of the liquid phase. The steam and multiple stages in the tower thus serve an important function, allowing the most dilute vapor phase concentration of unreacted materials to exist near the liquid product outlet, thus creating the largest driving force at this point for any last remaining residual unreacted materials to vaporize. This combination of features enables a higher degree of unreacted materials to be removed than what is achieved by prior processes.

In an embodiment of the invention, the reactor effluent is pre-heated to between 100 and 250° C., preferably 150 to 220° C., prior to entering the multiple-stage stripping device. The stripping device is maintained at a vacuum pressure ranging from 5 mmHg to 760 mmHg, and more typically from 100 mmHg to 500 mmHg The stripping steam to reactor effluent feed ratio can vary from 0.05 to 1, and typically from 0.09 to 0.25. The stripping steam may be supplied at a broad temperature and pressure range, and appropriate parameters may be selected by one skilled in the art in possession of this disclosure. Because the steam may introduce water into the process, a drier may be added to remove this water. The stripped product or any portion thereof, which may include unreacted aromatic compound and alkylating agent as well as monoalkylate product, may be recycled back into the alkylation reaction.

The continuous stripping step results in lower levels of residual unreacted materials in the product. In an embodiment of the invention, the amount of unreacted aromatic compound remaining in the product after the stripping step is less than 0.012 wt %, preferably less than 0.007 wt %, preferably less than 0.002 wt %, preferably less than 0.001 wt %, and preferably 0 wt %. Alternatively, the amount of unreacted aromatic compound remaining in the product after the stripping step is less than 100 ppm, preferably less than 80 ppm, preferably less than 60 ppm, preferably less than 40 ppm, preferably less than 20 ppm, preferably less than 10 ppm, and preferably 0 ppm. In an embodiment of the invention, the amount of unreacted alkylating agent remaining in the product after the stripping step is less than 0.8 wt %, preferably less than 0.5 wt %, preferably less than 0.25 wt %, preferably less than 0.1 wt %, and preferably 0 wt %. Alternatively, the amount of unreacted alkylating agent remaining in the product after the stripping step is less than 300 ppm, preferably less than 200 ppm, preferably less than 100 ppm, preferably less than 50 ppm, preferably less than 20 ppm, preferably less than 10 ppm, and preferably 0 ppm.

In an embodiment of the invention, the bromine number, a measurement of olefinic unsaturation remaining in the product, is no more than 1, preferably no more than 0.8, preferably no more than 0.6, preferably no more than 0.4, preferably no more than 0.3, and preferably no more than 0.2.

Alkylaromatic Compounds

The alkylaromatic compounds produced typically have the structures shown below:

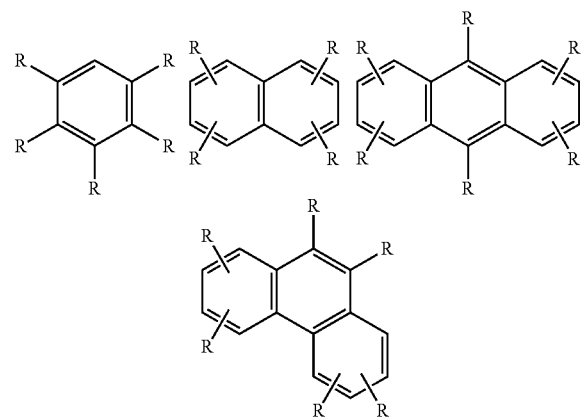

wherein at least one R group is the hydrocarbon residue of the alkylating agent. The remaining R groups are usually hydrogen or hydrocarbon groups such as cyclic or acyclic alkyl and alkenyl, aryl, $NH_2$, acylamido, halogen, acyl, alkoxycarbonyl, phenyl and YO or YS where Y is hydrogen, azyl, alkoxycarbonyl, phenyl, or cyclic or acyclic alkyl and alkenyl.

The alkylaromatic compounds produced are characterized by excellent thermal and oxidative stabilities, good additive solvency, and good seal compatibility while maintaining good VI and low temperature properties. These compounds are useful as lubricant basestocks and lubricant additives, such as dispersants, detergents, viscosity index improvers, extreme pressure and antiwear additives, antioxidants, pour point depressants, emulsifiers, demulsifiers, corrosion inhibitors, rust inhibitors, antistaining additives, friction modifiers, and the like.

EXAMPLES

The specific product composition of the reactor effluents was determined using Gas Chromatography, as generally described in "Modern Practice of Gas Chromatography," R. L. Grob and E. F. Barry, Wiley-Interscience, 3rd Edition (July 1995). When this disclosure indicates that the content of a component in the reactor effluent was 0.0 wt % or 0 ppm, the 0.0 wt % or 0 ppm is defined to mean that, if any of this component does exist in the reactor effluent, it is below the detection limit of the Gas Chromatography equipment and method used. Such detection limit, for purposes of this disclosure, is around 1 ppm or less. Additionally, the following test methods were used:

| | |
|---|---|
| Bromine number | ASTM D 1159 |
| Total acid number | ASTM D 974 |
| Kinematic viscosity | ASTM D 445 |
| Viscosity index | ASTM D 2270 |
| Flash point | ASTM D 92 |
| Pour point | ASTM D 97 |

Comparative Example 1

An alkylated naphthalene reactor effluent was preheated to about 95° C. and fed to a batch stripping device with a capacity of 9,550 gallons. The stripping device temperature and pressure were slowly increased to about 250° C. and a full vacuum of about 20 mmHg, respectively. After the lighter products were stripped, a representative sample from the product stream was taken and analyzed. The residual unreacted naphthalene content was 0.016 wt % and the residual unreacted olefin (alkylating agent) content was 0.9 wt %, based on the total wt % of the reactor effluent.

Comparative Example 2

Comparative Example 2 was identical to Comparative Example 1. A representative sample from the product stream contained a residual unreacted naphthalene content of 0.017 wt % and a residual unreacted olefin content was 1.0 wt %, based on the total wt % of the reactor effluent.

Comparative Example 3

Comparative Example 3 was identical to Comparative Example 1. A representative sample from the product stream contained a residual unreacted naphthalene content of 0.015 wt % and a residual unreacted olefin content was 0.8 wt %, based on the total wt % of the reactor effluent.

Comparative Example 4

Comparative Example 4 was identical to Comparative Example 1. A representative sample from the product stream contained a residual unreacted naphthalene content of 0.012 wt % and a residual unreacted olefin content was 0.8 wt %, based on the total wt % of the reactor effluent.

Example 1

An alkylated naphthalene reactor effluent was preheated to about 185° C. and fed to a continuous stripping device. The stripping steam flow rate was 3,500 lbs/hr and the stripping steam to feed ratio was 0.14. The stripping steam was supplied at a pressure of about 130 psig (7483 mmHg) and a temperature of about 356° F. (180° C.). The stripping device was maintained at a vacuum pressure of 140 mmHg After the lighter products were stripped, the main product stream was fed to a drying tower that was at a vacuum pressure of 10 mmHg Following this, a representative sample from the product stream was taken and analyzed. Surprisingly, the residual unreacted naphthalene content was 0.0 wt % and the residual unreacted olefin (alkylating agent) content was 0.0 wt %, based on the total wt % of the reactor effluent.

Examples 2 and 3

Examples 2 and 3 were identical to Example 1. A representative sample from the product stream from Example 2 was found to contain a residual unreacted naphthalene content of 0.0 wt % and a residual unreacted olefin content was 0.1 wt %, based on the total wt % of the reactor effluent. A representative sample from the product stream from Example 3 was found to contain a residual unreacted naphthalene content of 0.0 wt % and a residual unreacted olefin content was 0.0 wt %, based on the total wt % of the reactor effluent.

Relevant data from Comparative Examples 1-4 and Examples 1-3 is summarized in Table 1 below.

TABLE 1

Analysis of Product Streams from Comparative Examples 1-4 and Examples 1-3 After Stripping

|  | Comp Ex 1 | Comp Ex 2 | Comp Ex 3 | Comp Ex 4 | Ex 1 | Ex 2 | Ex 3 |
|---|---|---|---|---|---|---|---|
| Strip Method | Batch | Batch | Batch | Batch | Continuous | Continuous | Continuous |
| Bromine Number |  |  |  |  | 0.3 | 0.3 | 0.4 |
| Total Acid Number |  |  |  |  | 0.02 | 0.01 | 0.01 |
| Kinematic Viscosity, 40° C. |  |  |  |  | 28.8 | 28.0 | 28.0 |
| Kinematic Viscosity, 100° C. |  |  |  |  | 4.84 | 4.76 | 4.76 |
| Flash Point |  |  |  |  | 229° C. | 250° C. | 232° C. |
| Pour Point |  |  |  |  | −39° C. | −39° C. | −48° C. |
| Viscosity Index |  |  |  |  | 83 | 81 | 80 |
| Unreacted Naph, wt % | 0.016 | 0.017 | 0.015 | 0.012 | 0.0 | 0.0 | 0.0 |
| Unreacted Olefin, wt % | 0.9 | 1.0 | 0.8 | 0.8 | 0.0 | 0.1 | 0.0 |

What is claimed is:

1. A process comprising:
    a. contacting an aromatic compound selected from naphthalene, methylnaphthalenes, and other substituted naphthalenes, an alkylating agent, and a catalyst in a suitable reactor to produce an effluent stream comprising an alkylaromatic compound, a monoalkylated product differing from the alkylaromatic compound, unreacted aromatic compound and unreacted alkylating agent;
    b. heating said effluent stream to between 100 and 250° C.;
    c. in a stripping device maintained at a vacuum pressure of 5 mmHg to 760 mmHg, stripping said heated effluent stream in the presence of steam, wherein the steam to effluent stream feed ratio is from 0.05 to 1;
    d. separating a stripping stream from said stripping device, said stripping stream rich in the monoalkylated product, unreacted aromatic compound and unreacted alkylating agent; and
    e. separating a product stream from said stripping device, said product stream rich in the alkylaromatic compound and further having an unreacted aromatic compound content of less than 0.007 wt %, an unreacted alkylating agent content of less than 0.25 wt %, and a bromine number of 0.4 or less.

2. The process of claim 1 wherein the amount of unreacted aromatic compound in said product stream is 0 wt %.

3. The process of claim 1 wherein the amount of unreacted alkylating agent remaining in said product stream is 0 wt %.

4. The process of claim 1 wherein the alkylating agent is selected from at least one of 1-dodecene, 1-tetradecene, and 1-hexadecene.

5. The process of claim 1 wherein at least a portion of the stripping stream is recycled back into the reactor.

6. The process of claim 1 wherein the product stream has a kinematic viscosity at 100° C. according to ASTM Standard D 445 between 2 cSt and 100 cSt.

* * * * *